(12) United States Patent
Bödiger et al.

(10) Patent No.: US 6,683,223 B2
(45) Date of Patent: Jan. 27, 2004

(54) FLUIDISED BISPHENOL DUST

(75) Inventors: Michael Bödiger, League City, TX (US); Rainer Neumann, Krefeld (DE); Nikolai Kostyszyn, Kempen (DE); Rolf Lanze, Krefeld (DE); Frieder Heydenreich, Düsseldorf (DE); Michael Prein, Brasschaat (BE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/168,421

(22) PCT Filed: Dec. 11, 2000

(86) PCT No.: PCT/EP00/12482

§ 371 (c)(1),
(2), (4) Date: Oct. 15, 2002

(87) PCT Pub. No.: WO01/47851

PCT Pub. Date: Jul. 5, 2001

(65) Prior Publication Data

US 2003/0144560 A1 Jul. 31, 2003

(30) Foreign Application Priority Data

Dec. 23, 1999 (DE) .......................................... 199 62 530

(51) Int. Cl.$^7$ ................................................ C07C 39/16
(52) U.S. Cl. ....................................... 568/728; 568/727
(58) Field of Search ................................. 568/728, 727

(56) References Cited

U.S. PATENT DOCUMENTS 2,775,620 A    12/1956   Williamson ................. 260/619

FOREIGN PATENT DOCUMENTS

| CH | 493445 | 7/1990 |
| EP | 0 278 246 | 8/1988 |
| EP | 0 342 758 | 5/1989 |

*Primary Examiner*—Michael L. Shippen
(74) *Attorney, Agent, or Firm*—Joseph C. Gil; Aron Preis

(57) ABSTRACT

A process for fluidizing bisphenol dust is disclosed. The process entails adding 0.1 to 10 parts by weight of water per 1 part by weight of bisphenol dust. Also disclosed is a process for preparing a bisphenol wherein the fluidized bisphenol dust according to the invention is introduced before, during or after reaction of a phenol with a carbonyl compound.

6 Claims, 1 Drawing Sheet

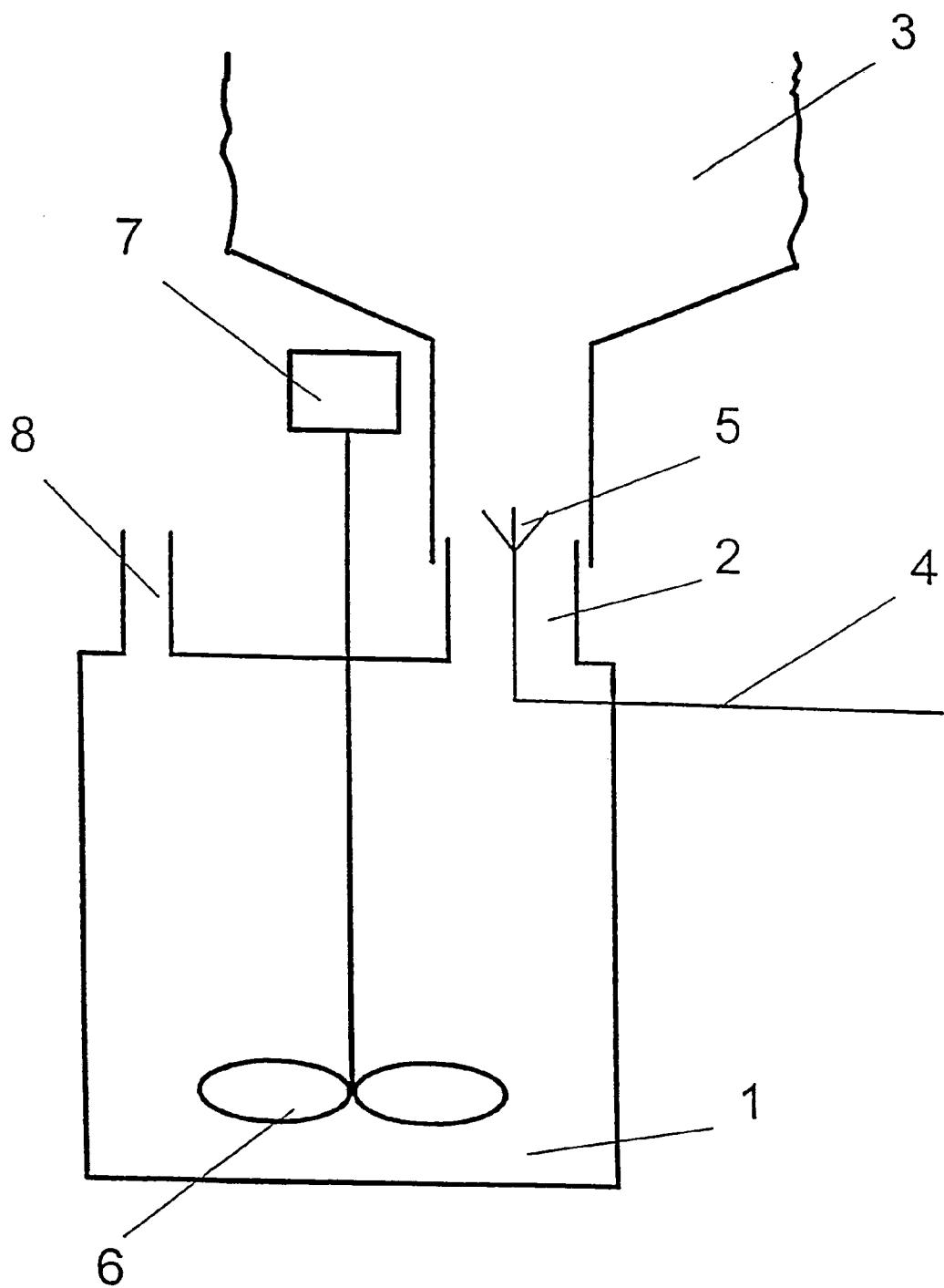

FLUIDISED BISPHENOL DUST

The present invention provides fluidised bisphenol dust containing bisphenol dust and water, a process for preparing this and a process for preparing a bisphenol, wherein fluidised bisphenol dust is supplied to the process.

Bis(4-hydroxyaryl)alkanes, called bisphenols in the following, are important as starting materials or as intermediates for preparing a large number of commercial products. Bisphenols can be prepared by the condensation of phenols and carbonyl compounds. Substituted or unsubstituted phenols may be used.

The condensation product from the reaction between phenol and acetone, 2,2-bis(4-hydroxyphenyl)propane (bisphenol A, BPA), is of particular industrial importance. BPA is used as the starting material for preparing many different types of polymer materials such as, for example, polyarylates, polyetherimides, polysulfones and modified phenol/formaldehyde resins. Preferred areas of application include the preparation of epoxy resins and polycarbonates.

Processes for preparing bisphenols by acid catalysed reaction of phenols with carbonyl compounds are known, for example, from U.S. Pat. No. 2,775,620 and EP-A-0 342 758.

Bisphenols of the general structure may be prepared by processes which are analogous to the processes for preparing BPA.

Bisphenols and in particular bisphenol A are advantageously converted into the form of so-called prills (prills are spherical solid particles which may be prepared by solidifying molten droplets in a stream of gas) or flakes. This enables simple storage, simple transport and simple handling procedures.

When producing bisphenol prills and bisphenol flakes or when otherwise handling bisphenols, a fine bisphenol dust is produced which consists of high purity bisphenol. The dust is tacky and difficult to handle. Handling this dust involves the risk of dust explosions. For this reason, the bisphenol dust is usually disposed of and, for example, incinerated, which entails a costly manual handling procedure and extensive safety precautions due to the risk of dust explosions. This has the disadvantage that disposal of the dust represents destruction of the valuable raw material bisphenol and in addition this procedure is not economically viable due to the high handling costs.

The present invention is therefore based on the object of providing a process for simplifying the handling of bisphenol dust and the possibility of making economic use of the dust.

This object is achieved by the provision of a process for fluidising bisphenol dust. This process enables the supply of bisphenol dust to the process for preparing bisphenols.

Thus, the invention provides a process for fluidising bisphenol dust, consisting of adding 0.1 to 10 parts by weight of water per 1 part by weight of bisphenol dust.

The invention also provides fluidised bisphenol dust containing 0.1 to 10 parts by weight of water per 1 part by weight of bisphenol dust.

The invention also provides a process for preparing a bisphenol, wherein fluidised bisphenol dust containing 0.1 to 10 parts by weight of water per 1 part by weight of bisphenol dust is supplied to the process before, during or after reaction of a phenol with a carbonyl compound.

Bisphenols in accordance with the invention are any bisphenols at all. Bisphenol A is preferred.

Phenols in accordance with the invention are any substituted phenols at all, unsubstituted phenol being preferred.

Carbonyl compounds in accordance with the invention are any carbonyl compounds at all. Acetone is preferred.

The amount of water used according to the invention is 0.1 to 10 parts by weight, preferably 0.15 to 1 part by weight, particularly preferably 0.2 to 0.4 parts by weight per 1 part by weight of bisphenol.

The fluidised bisphenol dust may preferably be supplied to the process for preparing a bisphenol without removing the water.

The fluidised bisphenol dust is preferably dissolved, preferably in a phenol, before being supplied to the process for preparing a bisphenol. This phenol is preferably the same phenol which is used in the process for preparing the bisphenol.

Supplying the fluidised bisphenol dust to the process for preparing a bisphenol may take place at any point during the process for preparing the bisphenol. Supply preferably takes place at the crystallisation stage in the process for preparing a bisphenol. Another preferred embodiment of the process is that in which supply of the fluidised bisphenol dust takes place at the mother liquor dewatering stage in the process for preparing the bisphenol.

In a preferred embodiment of the present invention, the bisphenol dust has a particle size of less than 1 mm, particularly preferably of less than 0.5 mm, very particularly preferably of less than 50 $\mu$m.

According to the invention, the particles which form the bisphenol dust may have any shape at all. They preferably have the form of fragments of geometric shapes, for example fragments of platelets or spheres.

According to the invention, fluidisation is understood to be production of the ability to flow. The ability to flow in this connection means, for example, that the fluidised bisphenol dust, under the effects of only the force of gravity, flows through a 50 cm long tube with a diameter of 20 cm at a sufficiently rapid rate, preferably at a rate greater than 300 kg per 10 minutes.

Bisphenol dust according to the invention preferably has a purity of greater than 95 wt. %.

Bisphenol dust according to the invention may also contain isomers and secondary products which are produced during the preparation of bisphenol.

In particular, so-called "start-up material", which is produced in the form of a dust when starting up bisphenol A preparation, is also to be included within the expression bisphenol dust.

The process according to the invention for preparing a bisphenol, wherein fluidised bisphenol dust is supplied to the process before, during or after reaction of a phenol with a carbonyl compound, is preferably performed in such a way that the amount of bisphenol dust supplied to the process is substantially less than the amount of bisphenol produced overall by the process. The amount of bisphenol dust supplied is preferably less than 10% of the amount of bisphenol prepared by the process.

The process according to the invention has a number of advantages. The bisphenol dust fluidised with water does not emit any dust to the surrounding atmosphere when it is handled, as does the same non-fluidised bisphenol dust when it is handled. This means that there is no longer any risk of dust explosions. As a result of the possibility of supplying the fluidised bisphenol dust to the process for preparing bisphenol, difficult and expensive waste disposal of the dust is not required. The valuable raw material bisphenol is recovered.

The process according to the invention for preparing BPA is preferably based on the acid catalysed reaction of phenol and acetone, wherein there is preferably a ratio by weight of phenol to acetone in the reaction of greater than 5:1. The acid catalysts used may be homogeneous or else heterogeneous Brönsted acids or Lewis acids, that is, for example, strong inorganic acids such as hydrochloric acid or sulfuric acid. Gel-like or macroporous sulfonated cross-linked polystyrene resins (acid ion-exchangers) are preferably used. The following details refer to a process for preparation which makes use of acid ion exchangers as catalysts.

In order to produce higher selectivity, the reaction of phenol and acetone may be performed in the presence of suitable mercapto compounds as co-catalysts. These may either be homogeneously dissolved in the reaction solution or be fixed to the sulfonated polystyrene matrix via ionic or covalent bonds. The reaction unit is preferably a layer bed or a fluidised bed which is flowed through either upwards or downwards, or a column of the reactive distillation column type.

When reacting phenol and acetone in the presence of acid catalysts and mercapto compounds as co-catalysts, a product mixture is produced which contains, apart from unreacted phenol and optionally acetone, primarily BPA and water. In addition small amounts of typical secondary products of the condensation also appear, that is, for example, 2-(4-hydroxyphenyl)-2-(2-hydroxyphenyl)propane (o,p-BPA), substituted indanes, hydroxyphenyl indanols, hydroxyphenyl chromanes, substituted xanthenes and more highly condensed compounds with three or more phenyl rings in the molecular structure.

The secondary products mentioned such as also water, phenol and acetone, may impair the suitability of the BPA for preparing polymers and have to be removed by suitable methods. High purity requirements are usually specified for the raw material BPA, in particular for preparing polycarbonate.

The working up and purification of BPA is usually performed by a multi-stage cascade of suitable purification processes such as, for example, suspension crystallisation, melt crystallisation, distillation and desorption. In an industrially preferred embodiment, the BPA is separated from the reaction mixture in the form of an approximately equimolar crystalline adduct with phenol by cooling the reaction mixture while the BPA/phenol adduct crystallises out. Crystallisation is preferably performed as suspension crystallisation. Suspension crystallisation is understood to be crystallisation from a liquid, wherein the crystals form a suspension with the liquid. The BPA/phenol adduct crystals are then separated from the liquid phase using suitable equipment for solid/liquid separation such as rotary filters or centrifuges and then subjected to further purification, if so required. The adduct crystals obtained have a purity of typically greater than 99 wt. % of BPA with respect to the secondary components, with a phenol content of about 40 wt. %. Impurities which adhere to the surface of the adduct crystals can be removed by washing with suitable solutions which typically contain one or more components from the group consisting of acetone, water, phenol, BPA and secondary components.

The liquid stream (mother liquor) produced during liquid/solid separation contains phenol, BPA, water produced during reaction and unreacted acetone and is enriched with the secondary components typically produced during the preparation of BPA. In a preferred embodiment, this mother liquor is recycled to the reaction unit. In order to maintain the catalytic activity of the acid ion exchanger, the water produced is first removed, preferably by distillation, wherein any acetone still present is optionally also removed from the mother liquor. The dewatered reaction stream obtained in this way is topped up with phenol and acetone and returned to the reaction unit. Alternatively, water and acetone may be entirely or partly removed by distillation before performing suspension crystallisation of the BPA/phenol adduct.

Some of the phenol present in the reaction solution may also be removed by distillation during the distillation steps mentioned above.

The problem with this type of circulatory mode of operation is that secondary products from BPA preparation are enriched in the circulation stream and can lead to deactivation of the catalyst system. In order to avoid excessive enrichment of secondary components in the circulation stream, some of the circulation stream, optionally after partial or complete recovery of phenol by distillation, is removed from the process chain as BPA resin.

In addition it has proved advantageous to pass some or the entire amount of the circulation stream through a rearrangement unit filled with acid ion exchanger after the solid/liquid separation stage and before or after the removal of water and residual acetone. This unit is generally operated at higher temperatures than the reaction unit. Some of the secondary components from BPA preparation present in the circulation stream are isomerised to BPA in this rearrangement unit under the conditions maintained there so that the overall yield of BPA can be increased.

The BPA/phenol adduct crystals obtained following suspension crystallisation of the reaction solution and solid/liquid separation, as described above, are taken to further purification steps if this is required, wherein the removal of phenol and optionally a reduction in the concentration of secondary components is achieved. The major proportion of the phenol is preferably removed.

Thus, the adduct crystals may be recrystallised, for example, from phenol, from organic solvents, from water or from mixtures of the previously mentioned compounds in accordance with a suspension crystallisation procedure. The phenol present in the adduct crystals may also be entirely or partly removed by the choice of a suitable solvent. Phenol optionally remaining in the BPA after recrystallisation may then be entirely removed by using suitable methods of distillation, desorption or extraction.

Alternatively, phenol may also be removed first from the adduct crystals. Preferred methods for this are desorption of the molten material using hot inert gases, vacuum distillation or a combination of the methods mentioned. It is possible to obtain BPA with a residual phenol content of less than 100 ppm from the adduct crystals in this way. By means of suitable reaction management and optionally the addition of stabilisers, the BPA is not broken down to any noticeable extent under the effects of the heat applied during the removal of phenol by distillation or by desorption.

Depending on the process conditions during suspension crystallisation from the reaction solution and the way solid/liquid separation and crystal growth are performed, BPA is obtained, after removal of phenol from the adduct crystals, which is suitable for preparing polymer materials. In particular for the preparation of high quality materials such as polycarbonate, it may be necessary to take the BPA obtained after the removal of phenol to a further purification operation Final purification may be performed by suspension crystallisation from water or suitable organic solvents, melt crystallisation in the form of a static or dynamic layer crystallisation process, extraction with water, aqueous neutral, acid or basic salt solutions or suitable organic solvents or in the form of a single-stage or multi-stage distillation process. By performing the purification operations mentioned, or a suitable combination of these, it is possible to obtain BPA with a purity greater than 99.9 wt. % which is particularly suitable for preparing high quality polymer materials.

In a preferred embodiment of the present invention, the bisphenol dust fluidised with water is converted in a vessel into which pure phenol or a phenol/water mixture has initially been introduced. If phenol/water mixtures are initially introduced, these preferably consist of a mixture with a ratio by weight of phenol to water of 9:1 to 1:9.

The present invention is explained in the following with reference to a drawing (FIG. 1). The drawing represents a preferred embodiment of the invention. The invention is not restricted to this preferred embodiment.

The bisphenol A dust is located in a storage container 3. This is a bag-like container made of a plastics fabric with a total internal volume of about 1 m$^3$ and with a discharge opening at the base. This storage container is called a "big bag". The discharge opening at the base of the big bag is pulled over opening 2 in storage tank 1. Water is sprayed in at the lower end of storage container 3, via pipe 4 which terminates in nozzle 5. This causes fluidisation of the bisphenol dust in storage container 3 and the dust falls into storage tank 1 under the effects of gravity. Storage tank 1 is provided with a stirrer 6 driven by a motor 7, by means of which the fluidised bisphenol dust can be homogenised. Nitrogen, as an inert gas, is supplied to the system via opening 8.

The invention is explained in the following by means of examples. The invention is not restricted to these examples.

EXAMPLE 1

According to the Invention 300 kg of bisphenol A dust which was produced during the preparation of bisphenol A prill, was located in a bag-like container made of a plastics fabric which had an opening at the base (so-called big bag). The big bag had a volume of about 1 m$^3$. A total of 80 l of water were supplied via a nozzle in the opening at the bottom end of the big bag, in a arrangement in accordance with FIG. 1. After only 5 minutes, the big bag had almost completely emptied into the inertised tank. Then 1000 kg of phenol at a temperature of 65° C. were placed in the tank and the heating jacket on the tank was turned on. The stirrer was switched on and the fluidised bisphenol A dust was dissolved completely. The solution produced was fed directly to the crystallisation stage of the process for preparing bisphenol A.

EXAMPLE 2

Comparison Example

Trial no. 1 was repeated without supplying any water. Attempts were made to get the bisphenol A dust out of the big bag through the opening in the base by using mechanical procedures (shaking, banging on the wall of the big bag, mechanical pushing out of the bisphenol A dust by using rods inserted through the opened big bag). Even after 30 minutes of intensive work, a high proportion of the bisphenol A dust was still inside the big bag.

What is claimed is:

1. A process for fluidising bisphenol dust, consisting of adding 0.1 to 10 parts by weight of water per 1 part by weight of bisphenol dust.

2. A process according to claim 1, wherein the bisphenol dust is bisphenol A dust.

3. Fluidised bisphenol dust containing 0.1 to 10 parts by weight of water per 1 part by weight of bisphenol dust.

4. Fluidised bisphenol A dust containing 0.1 to 10 parts by weight of water per 1 part by weight of bisphenol A dust.

5. A process for preparing a bisphenol, wherein fluidised bisphenol dust according to claim 3 is supplied to the process before, during or after reaction of a phenol with a carbonyl compound.

6. A process according to claim 5, wherein the bisphenol dust is bisphenol A dust and the phenol is unsubstituted phenol and the carbonyl compound is acetone.

* * * * *